United States Patent [19]

Shroot et al.

[11] Patent Number: 4,983,625

[45] Date of Patent: Jan. 8, 1991

[54] PSORALENE-BASED BATH COMPOSITIONS FOR TREATMENT OF SKIN DISORDERS

[75] Inventors: Braham Shroot; Josiane Allec, both of Antibes, France

[73] Assignee: Centre International de Recherches Dermatologiques (CIRD), Valbonne, France

[21] Appl. No.: 324,130

[22] Filed: Mar. 16, 1989

Related U.S. Application Data

[63] Continuation-in-part of Ser. No. 145,046, Jan. 19, 1988, abandoned, which is a continuation of Ser. No. 845,836, Mar. 28, 1986, abandoned.

[30] Foreign Application Priority Data

Apr. 1, 1985 [LU] Luxembourg .............................. 85829

[51] Int. Cl.⁵ .............................................. A61K 31/35
[52] U.S. Cl. .................................... 514/455; 514/863
[58] Field of Search .................................. 514/455, 863

[56] References Cited

PUBLICATIONS

Hannuksela et al.,–Br. J. Dermat (1978), 99, 703–.
Salo et al., Acta Dermaouener, 61:551–554, 1981.
Jansen et al.–Acta Dermatouener, 62:317–370, 1982.
Fischer et al.–Acta Dermatouener, 56:383–390, 1976.
Balsam et al., "Cosmetics, Sci & Tech", 2nd ed, vol. 2, pp. 503–514. (1972).

*Primary Examiner*—Leonard Schenkman
*Attorney, Agent, or Firm*—Cushman, Darby & Cushman

[57] ABSTRACT

A bath composition for the treatment of psoriasis or other cutaneous disorders contains from 10–79.9 weight percent of a hydrophilic phase, from 20–89.9 weight percent of a fatty or lipophilic phase and from 0.1–2 weight percent of an active component belonging to the class of psoralenes.

9 Claims, No Drawings

PSORALENE-BASED BATH COMPOSITIONS FOR TREATMENT OF SKIN DISORDERS

This application is a continuation-in-part of application Ser. No. 07/145,046, filed Jan. 19, 1988, which in turn is a continuation of application of application Ser. No. 06/845,836 filed Mar. 28, 1986 both abandoned.

The present invention relates to a bath composition for use in the photochemic therapeutic treatment of psoriasis and other cutaneous disorders such as fungal mycosis and vitiligo wherein the active component of said composition belongs to the class of psoralene compounds.

The treatment of psoriasis using a psoralene bath, followed by UV radiation (PUVA treatment) has been known for a number of years and provides excellent results without encountering the disadvantages of a topical application of a psoralene-based solution or cream.

The following articles describe more particularly the use of trioxsalen baths for use in such treatments.

M. Hannuksela et al, Brit. Journal of Dermatology, (1978) 99, p. 703-707;

O. P. Salo et al, Acta Dermatovener 61:551-554, 1981 and

C. T. Jansen et al, Acta Dermatovener 62:317-320, 1982.

With regard to these known treatments, psoralene baths have the advantage of providing uniform application of the active substance on all parts of the body which permits a reduction of the exposure time to UV rays.

One disadvantage caused by this treatment, which occasionally traumatizes certain patients, is manifested by a pronounced drying sensation of the epidermis, due not only to the treatment but also to the very nature of the disorder.

With a view to palliate this drying effect of the skin, it is current practice to apply after each treatment session of the body an oily product, most often petrolatum, as has been described by T. Fisher et al, Acta Dermatovener 56:3383-386, 1976.

The subsequent application of an oily product complicates the treatment without providing totally satisfactory results. The present invention, on the other hand, proposes the use of a bath composition, the active component of which is a psoralene, which composition reduces skin dryness without requiring the use of a subsequent application of an oily product.

The composition, according to the present invention, which is diluted at time of use in the bath water, provides, because its essential components, a single stage treatment wherein not only is a skin re-oiling agent more easily uniformly applied and distributed over the skin but also the solubilization of psoralenes is enhanced.

The present invention thus relates to a bath composition for use in the treatment of psoriasis and other cutaneous disorders, said composition being provided in the form of an oily product and comprising from 10 to 79.1 percent by weight of a hydrophilic phase, from 20 to 89.9 weight percent of a lipophilic or fatty phase, and from 0.1 to 2 weight percent of an active component belonging to the class of psoralenes.

By the expression "active component belonging to the class of psoralenes" is meant, not only psoralene itself and it isomers such as angelicine, but also their various derivatives, and more particularly compounds having the formula

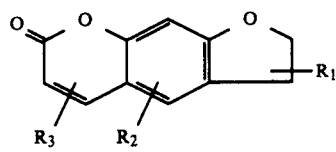

wherein $R_1$, $R_2$ and $R_3$ each independently represent hydrogen branched or straight chain lower alkyl, —$COOR_4$ or —$OR_5$, wherein $R_4$ is lower alkyl and $R_5$ is hydrogen or lower alkyl.

Representative compounds having the above formula include:
8-methoxy psoralene (methoxsalen),
5-methoxy psoralene (bergapten),
4,5', 8-trimethyl psoralene (trioxsalen) and
3-carbethoxy psoralene.

The hydrophilic phase of the composition according to the present invention represents, preferably, from 14 to 56 weight percent of the total weight of the composition and comprises at least one hydrophilic agent selected from the group consisting of:
(i) lauryl alcohol polyoxyethylenated and/or polyoxypropylenated with 2 to 5 moles of ethylene oxide and/or propylene oxide,
(ii) polyoxyethylenated fatty ester of glycerol with 5 to 10 moles of ethylene oxide, and
(iii) sorbitan and/or sorbitol monolaurate polyoxyethylenated with 2 to 5 moles of ethylene oxide.

These compounds are provided at ambient temperature either under liquid form or in the form of a fluid paste.

Among the above compounds the most suitable according to the invention are as follows:

lauryl alcohol polyoxyethylenated with 2 moles of ethylene oxide, sold under the trade name "DEHYDOL LS2" by Henkel, lauryl alcohol polyoxyethylenated with 5 moles of ethylene oxide and polyoxypropylenated with 5 moles of propylene oxide, sold under the trade name "AETHOXAL B" by Henkel, lauryl alcohol polyoxyethylenated with 4 moles of ethylene oxide, sold under the trade name "BRIJ 30" by Atlas, lauryl alcohol polyoxyethylenated with 2 moles of ethylene oxide, sold under the trade name "MERGITAL LM2" by Henkel, glycerol cocoate polyoxyethylenated with 7 moles of ethylene oxide, sold under the trade name "CETIOL HE" by Henkel, and sorbitan and sorbitol monolaurate polyoxyethylenated with 4 moles of ethylene oxide, sold under the trade name "TWEEN 21" by Atlas. The lipophilic phase of the bath composition of the present invention represents, preferably, from 30 to 85.8 weight percent based on the total weight of the composition.

Although this lipophilic phase can comprise any cosmetically acceptable oil, preferably there is employed, in accordance with the present invention, one or more of the following components:

1. esters of fatty acids and/or alcohols, such as decyloleate sold under the trade name "CETIOL V" by Henkel, isocetyl stearate sold under the trade name "CRODAMOL ICS" by Croda, and isopropyl myristate;

2. fatty alcohols, saturated or unsaturated, branched or not, and principally 2-octyldodecanol sold under the trade name "EUTANOL G" by Henkel;

3. fatty acids, saturated or unsaturated, such as oleic acid;

4. hydrocarbons such as petrolatum oil;

5. mono-, di- or triglycerides of fatty acids and principally the triglycerides of caprylic/capric acids, sold under the trade name "MIGLYOL 812" by Dynamit Nobel or vegetable oils such as ricin oil.

The hydrophilic phase of the bath composition according to the present invention can optionally contain fatty amides such as the diethanolamide of linoleic acid sold under the trade name "COMPERLAN F" by Henkel or even the mono- or di-ethanolamides of the coconut fatty acids. The amides improve not only the compatibility of the various hydrophilic/lipophilic components but also the feel of the oil in the bath.

If desired, a foaming effect can be imparted to the bath composition of the present invention by incorporating therein from 0.5 to 25 percent by weight of an anionic surface active agent.

Representative preferred surface active agents include, principally, the alkyl ether phosphates of polyoxyethylenated fatty alcohols.

The bath composition of the present invention can also include an adjuvant to improve the solubility of psoralene in water. This solubilization agent can be selected from the group consisting of acetone, ethanol or polyols such as polyethylene glycol, polypropylene glycol or glycerol. This solubilization agent is generally present in an amount less than or equal to 25 weight percent based on the total weight of the bath composition.

The treatment of psoriasis, and other cutaneous disorders, using the composition of the present invention comprises, at the time of use, admixing with a bath containing from 100 to 150 liters of water, from 0.5 to 3 g of the bath composition of this invention per liter of bath water. This corresponds to a psoralene concentration of 0.5 to 60 mg/liter.

After thoroughly mixing the bath composition of the present invention with he bath water, the bath has a homogeneous milky appearance. The patient remains in this bath for a period of time ranging from 5 to 30 minutes, taking care to avoid splashing any of the bath on the face and especially in the eyes.

After remaining in the bath for the prescribed period of time, the patient is exposed to UV rays for a short period of time, using lamps that emit from 5 to 15 mW/cm$^2$, preferably from 11 to 12 mW/cm$^2$. In a typical treatment, the patient receives a dosage of 0.1 J/cm$^2$ during the first session, with an approximate irradiation duration of 8 seconds, the doses being progressively increased up to 3 to 10 J cm$^2$ according to the skin type.

The average treatment for an 80% improvement in the state of the patient's skin, is 20 sessions, at a rate of 3 sessions per week. Thereafter a maintenance treatment is instituted by progressively reducing the frequency of the sessions to twice a week, then once a week, and finally once every two weeks.

The following non-limiting examples of bath compositions are provided to illustrate the present invention.

EXAMPLE 1

| | |
|---|---|
| Lauryl alcohol polyoxyethylenated with 2 moles of ethylene oxide sold under the trade name "DEHYDOL LS 2" by Henkel | 11.4 g |
| Glycerol cocoate polyoxyethylenated with 7 moles of ethylene oxide sold under the trade name "CETIOL HE" by Henkel | 5.7 g |
| Lauryl alcohol polyoxyethylenated with 5 moles of ethylene oxide and polyoxypropylenated with 5 moles of propylene oxide, sold under the trade name "AETHOXAL B" by Henkel | 31.5 g |
| Decyl oleate sold under the trade name "CETIOL V" by Henkel | 7.6 g |
| Petrolatum oil | 22.812 g |
| Ethanol, 95% | 8.5 g |
| Acetone | 8.5 g |
| Propylene glycol | 3.8 g |
| 5-methoxy psoralene | 0.188 g |

EXAMPLE 2

| | |
|---|---|
| Sorbitan and sorbitol monolaurate polyoxyethylenated with 4 moles of ethylene oxide sold under the trade name "TWEEN 21" by Atlas | 7 g |
| Glycerol cocoate polyoxyethylenated with 7 moles of ethylene oxide sold under the trade name "CETIOL HE" by Henkel | 19 g |
| Isocetyl isostearate sold under the trade name "CRODAMOL ICS" by Croda | 21 g |
| Isopropyl myristate | 21 g |
| Petrolatum oil | 21.7 g |
| Diethanolamide of linoleic acid sold under the trade name "COMPERLAN F" by Henkel | 10 g |
| 8-methoxy psoralene | 0.3 g |

EXAMPLE 3

| | |
|---|---|
| Lauryl alcohol polyoxyethylenated with 4 moles of ethylene oxide sold under the trade name "BRIJ 30" by Atlas | 25 g |
| Squalene | 74.9 g |
| 8-methoxy psoralene | 0.1 g |

EXAMPLE 4

| | |
|---|---|
| Lauryl alcohol polyoxyethylenated with 2 moles of ethylene oxide, sold under the trade name "MERGITAL LM2" by Henkel | 20 g |
| Glycerol cocoate polyoxyethylenated with 7 moles of ethylene oxide, sold under the trade name "CETIOL HE" by Henkel | 28 g |
| Isocetyl isostearate sold under the trade name "CRODAMOL ICS" by Croda | 26 g |
| Petrolatum oil | 25.7 g |
| 8-methoxy psoralene | 0.3 g |

EXAMPLE 5

| | |
|---|---|
| Lauryl alcohol polyoxyethylenated with 4 moles of ethylene oxide sold under the trade name "BRIJ 30" | 25 g |

| | |
|---|---|
| by Atlas | |
| Triglycerides of capric/caprylic acids sold under the trade name "MIGLYOL 812" by Dynamit Nobel | 37.82 g |
| Petrolatum oil | 37.00 g |
| 8-methoxy psoralene | 0.180 g |

What is claimed is:

1. A bath composition, for use in the treatment of psoriasis and other cutaneous disorders, said composition being in the form of an oily product and comprising
   (a) 10 to 79.9 weight percent of a hydrophilic phase comprising a hydrophilic agent selected from the group consisting of
      (i) lauryl alcohol polyoxyethylenated and/or polyoxypropylenated with 2 to 5 moles of ethylene oxide and/or propylene oxide,
      (ii) polyoxyethylenated fatty ester of glycerol with 5 to 10 moles of ethylene oxide,
      (iii) sorbitan and/or sorbitol monolaurate polyoxyethylenated with 2 to 5 moles of ethylene oxide, and
      (iv) a mixture of at least two of (i)-(iii), above,
   (b) 20 to 89.9 weight percent of a lipophilic phase comprising a lipophilic agent selected from the group consisting
      (1') ester of a fatty alcohol,
      (2') ester of a fatty acid,
      (3') saturated fatty alcohol,
      (4') unsaturated fatty alcohol,
      (5') saturated fatty acid,
      (6') unsaturated fatty acid,
      (7') a hydrocarbon,
      (8') monoglyceride of a fatty acid,
      (9') diglyceride of a fatty acid,
      (10') triglyceride of a fatty acid and
      (11') a mixture of at least two of (1') to (10'), above, and
   (c) 0.1 to 2 weight percent of an active component having the formula

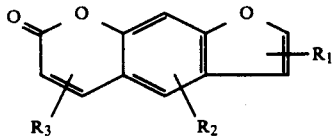

wherein
$R_1$, $R_2$ and $R_3$ each independently represent hydrogen, branched or straight chain lower alkyl, —COOR$_4$ or —OR$_5$, wherein $R_4$ is lower alkyl and $R_5$ is hydrogen or lower alkyl, said bath composition giving rise to a homogeneous milky appearance when mixed with water.

2. The bath composition of claim 1 wherein said hydrophilic agent is selected from the group consisting of:
   lauryl alcohol polyoxyethylenated with 2 moles of ethylene oxide,
   lauryl alcohol polyoxyethylenated with 5 moles of ethylene oxide and polyoxypropylenated with 5 moles of propylene oxide,
   lauryl alcohol polyoxyethylenated with 4 moles of ethylene oxide,
   lauryl alcohol polyoxyethylenated with 2 moles of ethylene oxide,
   glycerol cocoate polyoxyethylenated with 7 moles of ethylene oxide, and
   sorbitan and sorbitol monolaurate polyoxyethylenated with 4 moles of ethylene oxide.

3. The bath composition of claim 1 which also contains at least one anionic surface active agent present in an amount ranging from 0.5 to 25 percent by weight based on the total weight of said composition or a fatty amide.

4. The bath composition of claim 3 wherein said fatty amide is the diethanolamide of lauric acid or the mono- and diethanolamides of coconut fatty acids.

5. The bath composition of claim 1 wherein said active component is selected from the group consisting of psoralene, 8-methoxy psoralene, 5-methoxy psoralene, 4,5', 8-trimethyl psoralene and 3-carbethoxy psoralene.

6. The bath composition of claim 1 wherein said hydrophilic phase is present in an amount ranging from 14 to 56 weight percent based on the total weight of said composition.

7. The bath composition of claim 1 wherein said lipophilic phase is present in an amount ranging from 30 to 85.8 weight percent based on the total weight of said composition.

8. A method for treating a patient suffering from psoriasis or other cutaneous disorders comprising bathing said patient in a bath having a homogeneous milky appearance, said bath comprising an admixture of water and from 0.5 to 3 grams of the bath composition of claim 1 per liter of water, leaving the patient in said bath for a period of time ranging from 5 to 30 minutes and exposing the patient to UV rays.

9. The method of claim 8 wherein said patient is exposed to UV rays using lamps that emit from 5 to 15 mW/cm$^2$.